United States Patent [19]

Piper

[11] Patent Number: 5,533,502
[45] Date of Patent: Jul. 9, 1996

[54] POWDER INHALER WITH AEROSOLIZATION OCCURRING WITHIN EACH INDIVIDUAL POWDER RECEPTACLE

[75] Inventor: Samuel D. Piper, Sacramento, Calif.

[73] Assignee: Vortran Medical Technology, Inc., Sacramento, Calif.

[21] Appl. No.: 341,706

[22] Filed: Nov. 18, 1994

Related U.S. Application Data

[63] Continuation of Ser. No. 70,111, May 28, 1993, abandoned.
[51] Int. Cl.⁶ .......................... A61M 15/00; A61M 16/00; B05D 7/14; B65D 83/06
[52] U.S. Cl. ................... 128/203.21; 128/203.15
[58] Field of Search ................ 128/200.14, 203.12, 128/203.15, 203.19, 203.21, 203.23; 604/58; 222/636; 206/528

[56] References Cited

U.S. PATENT DOCUMENTS

| | | | |
|---|---|---|---|
| 2,549,303 | 4/1951 | Friden | 128/203.15 |
| 2,573,918 | 11/1951 | McCuiston | 128/203.15 |
| 4,627,432 | 12/1986 | Newell et al. | 128/203.23 |
| 4,884,565 | 12/1989 | Cocozza | 128/203.21 |
| 5,033,463 | 7/1991 | Cocozza | 128/203.21 |
| 5,035,237 | 7/1991 | Newell et al. | 128/203.15 |
| 5,113,855 | 5/1992 | Newhouse | 128/203.12 |
| 5,287,850 | 2/1994 | Haber et al. | 128/203.15 |
| 5,337,740 | 8/1994 | Armstrong et al. | 128/203.15 |

FOREIGN PATENT DOCUMENTS

| | | | |
|---|---|---|---|
| 0237507 | 9/1987 | European Pat. Off. | 128/203.15 |
| 4004904 | 9/1990 | Germany | 128/203.15 |
| 2041763 | 9/1980 | United Kingdom | 128/203.15 |

OTHER PUBLICATIONS

"Turbuhaler"; 1990; Astra Respiratory Brochure, Sweden.

*Primary Examiner*—Kimberly L. Asher
*Attorney, Agent, or Firm*—John P. O'Banion

[57] ABSTRACT

An apparatus for generating respirable aerosol internal to a selected one of a plurality of medicament receptacles (40) containing pre-measured amounts of powdered medicament is disclosed herein. The medicament receptacles (40) are disposed in a medicament carrier (38) contained within a housing (10), and are sealed from exposure to the outside environment. The medicament carrier (38) is preferably a ring-shaped member detachably coupled to a carriage (24) which can be rotated to any one of a plurality of selected positions. A pair of aerosolization conduits (54, 56) having ends capable of puncturing the seal (44) covering the medicament receptacle (40) selected by the patient are also provided. Compression of the cover (12) and the carriage (24) pushes the selected medicament receptacle (40) against the edges of the aerosolization conduits (54, 56) causing the aerosolization conduits to puncture the seal (44) and penetrate the medicament receptacle (40). The medicament is entrained in air drawn in through the air inlet conduit (54), and aerosolized medicament is delivered to the patient through the aerosol outlet conduit (56). Aerosolization occurs internal to the medicament receptacle which has the dual function of serving as an aerosolization chamber.

15 Claims, 5 Drawing Sheets

FIG. – 7

POWDER INHALER WITH AEROSOLIZATION OCCURRING WITHIN EACH INDIVIDUAL POWDER RECEPTACLE

CROSS REFERENCE TO RELATED APPLICATIONS

This is a continuation of application Ser. No. 08/070,111 filed on May 28, 1993, now abandoned.

BACKGROUND OF THE INVENTION

1. Field of the Invention

This invention pertains generally to devices for administering powdered medicament to a patient, and more particularly to an apparatus for aerosolizing powdered medicament internal to a medicament storage receptacle containing a prepackaged measured dose of medicament.

2. Description of the Background Art

The aerosolization and delivery of selected medicaments for inhalation deposition within the respiratory airways of the human lung is an important means of treating patients having lung diseases. Currently, aerosol therapy utilizes one of three primary methods for generation of respirable medicinal aerosols, namely (a) nebulization of aqueous solutions or suspensions containing the medicine using a pneumatic or ultrasonic nebulization nozzle, (b) forced dispersion of a spray of a volatile chlorofluorocarbon (such as Freon®) liquid propellant containing the medicine as particles in liquid solution or suspension using a metered-dose inhaler (MDI), and (c) dry aerosolization of a medicament powder.

The first two methods are extremely effective in the treatment of patients with lung diseases, and the MDI is particularly popular with patients because it is small, pocket-sized, and portable. Furthermore, the MDI does not require a separate supply of compressed gas or electrical power for operation, so it can be effectively used anywhere when aerosol treatment is required. Unfortunately, the use of chlorofluorocarbons is being discontinued as a result of concern over the damage that has been reported to the protective ozone shield found in the stratosphere of the earth's atmosphere. The popular MDI may be eliminated if no suitable propellant is developed.

Therefore, the most likely suitable alternative to the MDI lies with dry aerosolization of a medicament powder that has been finely divided into particles that are small enough to be in the respirable size range. There are various existing designs and types of powder aerosol delivery devices and powder inhalers, but they have not been popular for therapy because of many operational problems. Some dry powder aerosolization devices require electrical power and compressed air or gas to operate. The small portable powder inhalers that have been designed have a variety of operational shortcomings, so that their use is not popular. The primary problem with such devices is their inability to deliver a consistent dose of medicine to the patient. The amount of powdered medicament entrained in a flow of air varies, in many cases medicament which should be administered to the patient is retained within the device and wasted, aerosolization density varies, and considerable effort must be exerted by the patient in generating an air flow to entrain the medicament. Some powder delivery devices move the medicament from a storage region to an aerosolization region for entrainment. As a result of mechanical handling of the medicament, any exposed surface inside the device that has contact with the medicament will acquire some residual medicament resulting in accumulated losses. While some powder delivery devices have minimized the handling of medicament by the use of a disk-shaped configuration with "blister" packs, problems still exist due to the medicament falling or being moved into a separate aerosolization region. Other devices may fail to provide a powder aerosol of respirable particle size due to air velocity being insufficient for full aerosolization, or due to portions of the aerosolization region not receiving air whatsoever.

Therefore, there is a need for a device which can generate a measured and reproducible dosage of respirable aerosol of the desired medicament powder with each puff of the powder inhaler, without waste of medicine, losses in the dispensing device, or strenuous effort by the patient. The present invention solves those needs and eliminates the deficiencies in existing powder inhalation devices.

SUMMARY OF THE INVENTION

The present invention pertains to an apparatus for generating respirable aerosol from powdered medicament internal to a selected one of a plurality of medicament "pockets" or "blisters" contained on a rotatable carrier. Alternatively, the present invention could be used to deliver pressurized or volatile liquid medicaments.

By way of example and not of limitation, the apparatus includes a housing having a cover and a base. Positioned within a cavity in the base is a medicament carrier containing one or more miniature "pockets" or "blisters" which serve as receptacles for powdered medicament. The medicament carrier can be a cylinder, a flat strip, or the like but, in the preferred embodiment, is a generally circular ring-shaped member or disk. Each receptacle contains a pre-measured amount of medicament and is sealed with a thin layer of aluminum foil, plastic or the like to protect the medicament from the outside environment. The medicament carrier is preferably detachably coupled to a carriage which can be rotated about an axis extending coaxially through the carriage. Alternatively, the medicament carrier and carriage can be fashioned as an integral unit. The carriage is coupled to the base, and can be selectively positioned according to detents or the like. In addition, the carriage is slidably coupled to the base for axial movement between the cover and the base, with separation between the cover and the carriage being maintained by a spring.

The apparatus also includes a mouthpiece coupled to the cover, and a pair of aerosolization conduits extending though the mouthpiece and into the housing. One conduit is used as an air inlet conduit, and the other conduit is used as an aerosol outlet conduit. Each of the conduits is capable of puncturing the relatively thin seal covering the medicament receptacle selected by the patient and, if desired, can include a knife-like edge at one end to assist in puncturing the seal.

If the patient requires a dose of medicament, he or she rotates the carriage to position a selected one of the medicament receptacles for dispensing. The detents which selectively position the carriage in relation to the base also align the medicament receptacles with the aerosolization conduits. The patient then compresses the cover and carriage, thereby pushing the selected medicament receptacle against the ends of the aerosolization conduits. This causes the aerosolization conduits to puncture the seal and penetrate the medicament receptacle. In addition, "keys" or "teeth" in the carriage and cover engage to prevent rotational motion of the carriage when in the compressed position, as well as to align the aerosolization conduits in the selected medicament receptacle.

While the cover and carriage are still in a compressed position, the patient inserts the mouthpiece into his or her mouth and inhales. The powdered medicament is entrained in the air flow introduced into the air inlet conduit and delivered to the patient through the aerosol outlet conduit. Significantly, all aerosolization occurs internal to the medicament receptacle and, therefore, the patient receives a uniform and repeatable dosage of medicine without loss or waste in the device.

An object of the invention is to deliver medicament with a consistent amount of powder of respirable particle size range with minimum agglomeration.

Another object of the invention is to aerosolize medicament internal to the medicament storage receptacle.

Another object of the invention is to eliminate the need to move medicament to an aerosolization region prior to aerosolization.

Another object of the invention is to provide a device wherein the medicament storage receptacle also serves as an aerosolization chamber.

Another object of the invention is to aerosolize all of the medicament in the medicament storage receptacle.

Another object of the invention is to provide for delivery of uniform and repeatable doses of powdered medicament.

Another object of the invention is to protect medicament from contamination during handling and administration.

Another object of the invention is to keep medicament dry during handling and administration.

Another object of the invention is to prevent medicament from becoming hydroscopic.

Another object of the invention is to keep medicament sterile during handling and administration if required.

Another object of the invention is to provide a device with a replaceable medicament carrier.

Another object of the invention is to provide a device capable of administering multiples doses of medicament.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DESCRIPTION OF THE PREFERRED EMBODIMENTS

Referring more specifically to the drawings, for illustrative purposes the present invention is embodied in the apparatus generally shown therein. It will be appreciated that the apparatus may vary as to configuration and as to details of the parts without departing from the basic concepts as disclosed herein.

Figure 1:
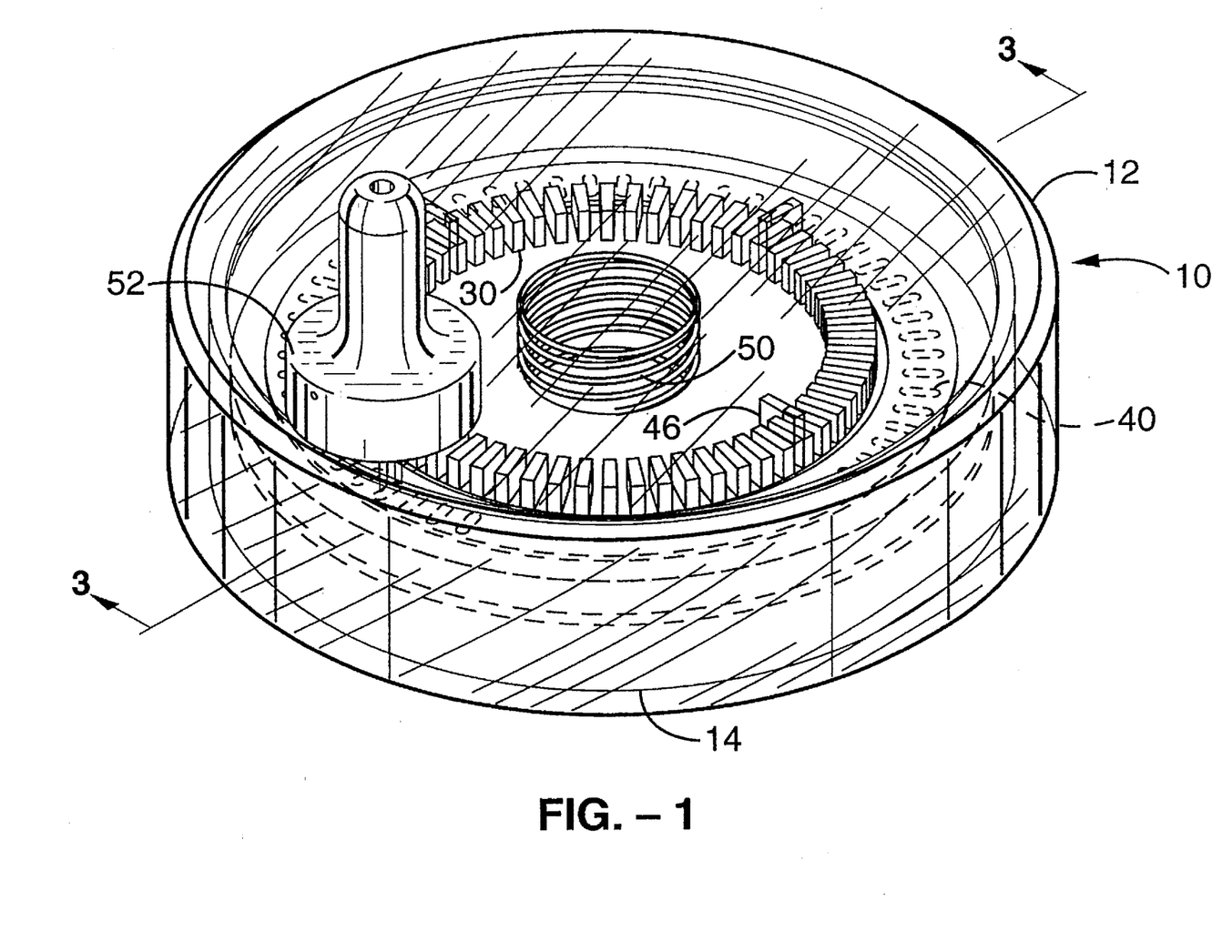
FIG. 1 is a perspective view of an apparatus according to the present invention.
Figure 2:
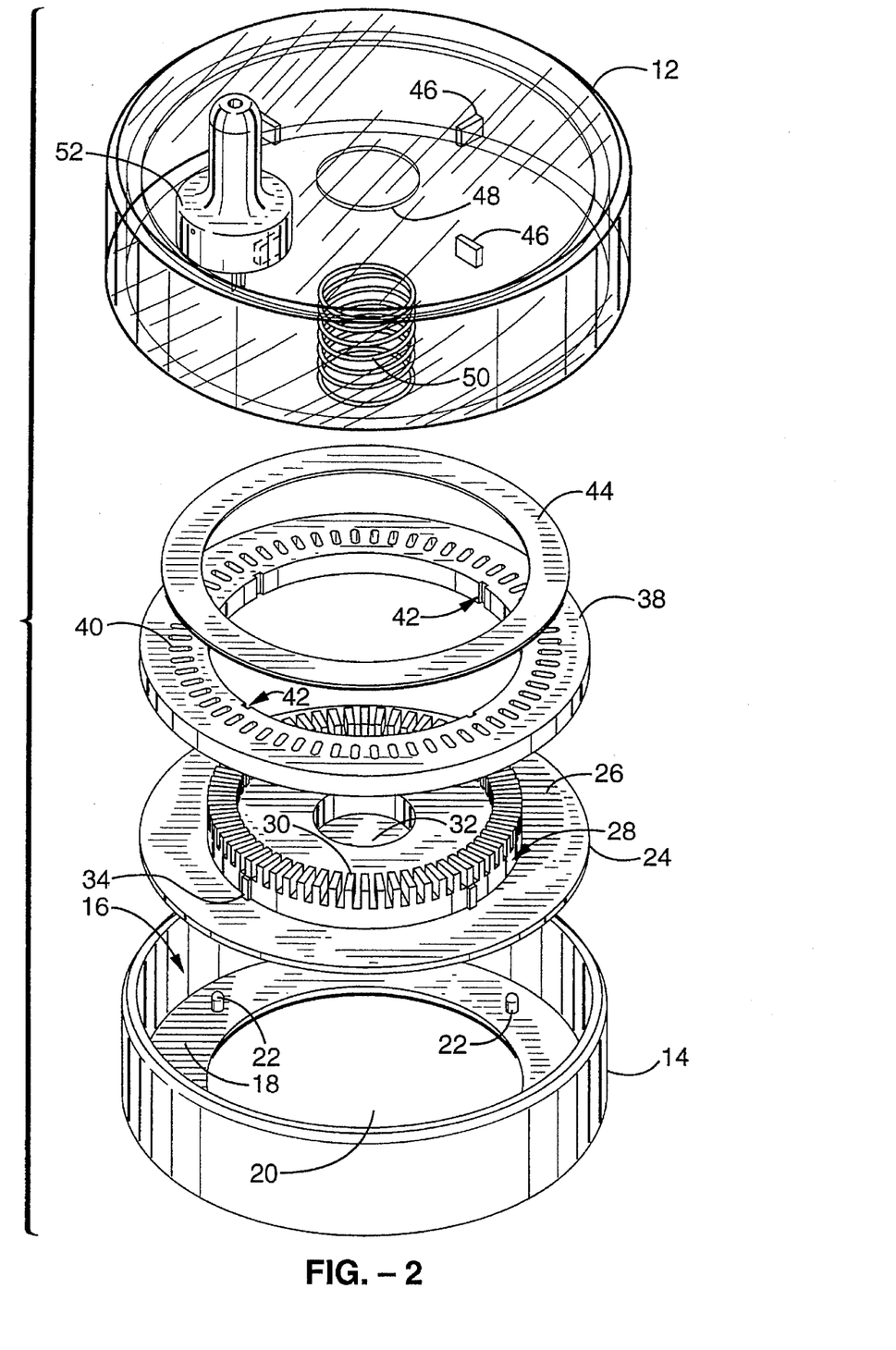
FIG. 2 is an exploded view of the apparatus shown in FIG. 1.

Referring to FIG. 1 and FIG. 2, an apparatus according to the present invention includes a housing 10 which is defined by a cover 12 and a base 14 which are detachably coupled in any conventional manner. While housing 10 is shown in the preferred embodiment as having a generally cylindrical shape, it should be noted that housing 10 can be fabricated in other shapes, the particular shape and size of housing 10 chosen being dependent upon such factors as aesthetics, convenience to the patient, and ease of handling. Included within base 14 is a cavity 16 which extends between a bottom wall 18 and the upper edge of base 14, an opening 20 extending coaxially through bottom wall 18, and a plurality of projections or nipples 22 projecting from bottom wall 18. In the preferred embodiment, there are four nipples 22, although the number can vary.

Figure 4:
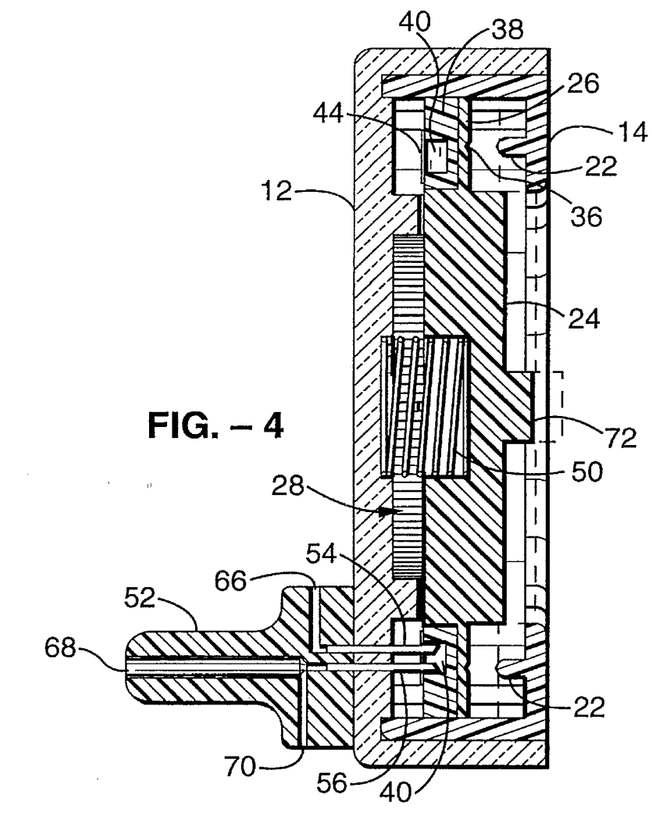
FIG. 4 is a cross-sectional view of the apparatus shown in FIG. 1 taken through line 3—3 which diagrammatically shows the carriage in a compressed position.

Disposed within cavity 16 is a generally circular carriage 24. Carriage 24 includes a carriage plate 26, a generally circular registration gear 28 having a plurality of spaced-apart teeth 30, a lower spring retention cavity 32 coaxially disposed in carriage 24, and a plurality of guide keys 34. The number of teeth 30 can vary but, in the preferred embodiment, there should be a sufficient number of teeth 30 to ensure positive registration of carriage 24 for each dosage of medicament as explained further below. Referring also to FIG. 4, positioned in the underside of carriage plate 24 are a plurality of detents 36 which are configured to mate with nipples 22. The number of detents 36 can vary but, in the preferred embodiment, there should be a sufficient number of detents 36 to ensure positive registration of carriage 24 for each dosage of medicament as explained further below.

A generally circular ring-shaped medicament carrier 38 includes a plurality of "pockets" or medicament receptacles 40 for containing medicament in powdered form, or in the form of a pressurized or volatile liquid. Medicament carrier 38 is generally planar, and includes a coaxially disposed opening through which registration gear 28 can extend. Medicament carrier 38 rests on carriage plate 26 and is secured in place rotationally by a plurality of keyways 42 configured to mate with guide keys 34. A seal 44, which can be fabricated from a thin layer of aluminum foil, plastic or the like affixed to medicament carrier 38 with a suitable adhesive material, seals medicament receptacles 40 from the environment. In the preferred embodiment, seal 44 is a ring-shaped structure but other shapes can be used. Alternatively, medicament receptacles 40 can be covered by separate, individual seals. Also, if desired, medicament receptacles 40 could be configured as "blisters" or "bubbles" extending from the surface of medicament carrier 38 instead of as "pockets" or "depressions" as shown.

Extending downward from the inside wall of cover 12 are a plurality of registration keys 46 configured to mate with the spaces between teeth 30 in registration gear 28. In the preferred embodiment, there are four registration keys 46, although the number can vary. Cover 12 also includes an upper spring retention cavity 48 coaxially disposed in its inside wall. When the apparatus is assembled, a spring 50 is seated in lower spring retention cavity 32 and upper spring retention cavity 48 and, therefore, extends between cover 12 and carriage 24. A mouthpiece 52 is coupled to the outer surface of cover 12 for administration of medicament to the patient.

Figure 3:
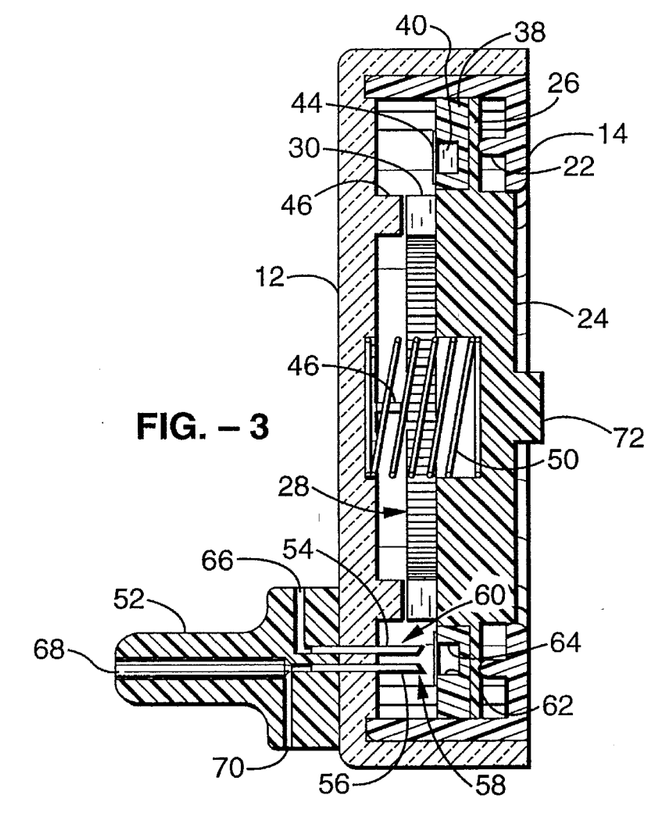
FIG. 3 is a cross-sectional view of the apparatus shown in FIG. 1 taken through line 3—3.

Referring also to FIG. 3 and FIG. 4, an air inlet conduit 54 and an aerosol outlet conduit 56, which are generally thin, cylindrical tubes, extend through cover 12 and into cavity 16. Air inlet conduit 54 and aerosol outlet conduit 56 are formed from any suitable material having sufficient rigidity to puncture seal 44. When carriage 24 is compressed in relation to cover 12, air inlet conduit 54 and aerosol outlet conduit 56 will puncture seal 44 and penetrate into medicament receptacle 40 as shown in FIG. 4. Preferably, the conduits and medicament receptacle 40 are aligned such that the outermost walls 58, 60 will generally abut the inside walls 62, 64 of medicament receptacle 40 during penetration.

Air inlet conduit 54 and aerosol outlet conduit 56 also extend into mouthpiece 52 where they communicate with an air inlet passage 66 and an aerosol outlet passage 68, respectively. Alternatively, the conduits could be molded into mouthpiece 52 or otherwise extend through mouthpiece 52 in any conventional manner. In operation, the patient places mouthpiece 52 in his or her mouth and inhales, thereby drawing in air through air inlet passageway 66. Medicament in medicament receptacle 40 is entrained in the air flow and dispensed to the patient though aerosol outlet passageway 68. In this manner, entrainment occurs internal to the medicament receptacle 40. In addition, the effectiveness of aerosolization can be increased by angling the ends of air inlet conduit 54 and aerosol outlet conduit 56 which extend into medicament receptacle 40 as shown. As a result, the opening in the ends of the conduits exposed to medicament will correctly direct the air flow and aerosol flow, and "bottoming" of the openings of the conduits in the medicament receptacle is prevented. Also, a secondary air port 70 extending into mouthpiece 52 and communicating with aerosol outlet passageway 68 can be provided. Secondary air port 70 will assist in the delivery of all of the aerosolized medicament to the patient (i) by reducing the amount of effort which must be exerted by the patient during inhalation, (ii) by providing for a secondary aerosolization process in aerosol outlet passageway 68, and (iii) if positioned tangentially in relation to the longitudinal axis through aerosol outlet passageway 68, will cause large particles to impinge on the walls of the passageway and be broken into smaller particles by creating a vortex or swirling effect.

As can be seen, therefore, medicament receptacle 40 not only serves as a container for medicament, but also as an aerosolization chamber. This configuration has the significant advantage of providing for aerosolizing medicament internal to a selected one of the medicament receptacles and delivering the aerosolized medicament to a patient without secondary handling. In addition, this configuration prevents non-aerosolized medicament from escaping from the medicament receptacle. As a result, medicament does not attach to the walls of a secondary aerosolization chamber as in prior devices, and aerosolization is complete within a medicament receptacle 40.

To operate the apparatus, the patient rotates carriage 24 using a knob 72 or the like until a selected one of the medicament receptacles 40 is aligned with the aerosolization conduits represented by air inlet conduit 54 and aerosol outlet conduit 56. In the preferred embodiment, there is one detent 36 corresponding to each medicament receptacle 40 and alignment is ensured when a detent 36 mates with a nipple 22. The patient then depresses carriage 24 or otherwise compresses carriage 24 in relation to cover 12, at which time registration keys 46 mate with the spaces between teeth 30 in registration gear 28. Engagement of registration keys 46 with registration gear 28 serves to prevent rotation of carriage 24 and to align the aerosolization conduits with the selected medicament receptacle during use. In the preferred embodiment, there is one tooth in teeth 30 for each medicament receptacle 40 so that alignment is maintained when carriage 24 is compressed. The patient continues to hold carriage 24 in the compressed position and inhales through mouthpiece 52, thereby aerosolizing medicament and receiving the predetermined dose. When the patient has received the dose, he or she releases carriage 24 which is returned to position by spring 50. The process is repeated when it is time to administer another dose of medicament. To assist the patient in delivery, a locking mechanism and release button (not shown) can be employed. In such an embodiment, once carriage 24 is compressed it would be held in place until the patient has inhaled the aerosol. This will ensure that the aerosolization conduits remain in medicament receptacle 40 during the administration of the medicament. Thereafter, the release button can be operated to return carriage 24 to its normal position. Additionally, a gear or ratcheting mechanism can be included so that carriage 24 is rotated to the next dose position upon release. In another embodiment, mouthpiece 52 and aerosolization conduits 54, 56 would be repositioned so that when the spring 50 is in its non-compressed position, the aerosolization conduits penetrate medicament receptacle 40. In such an embodiment, the patient would compress carriage 24 in order to select a particular medicament receptacle and then release carriage 24 for aerosolization and delivery.

In the embodiment heretofore presented, when all of the medicament has been administered, the patient can remove cover 12 from base 14 and replace medicament carrier 38. This embodiment provides for maximum utility and reuse of the apparatus by the patient.

Figure 5:
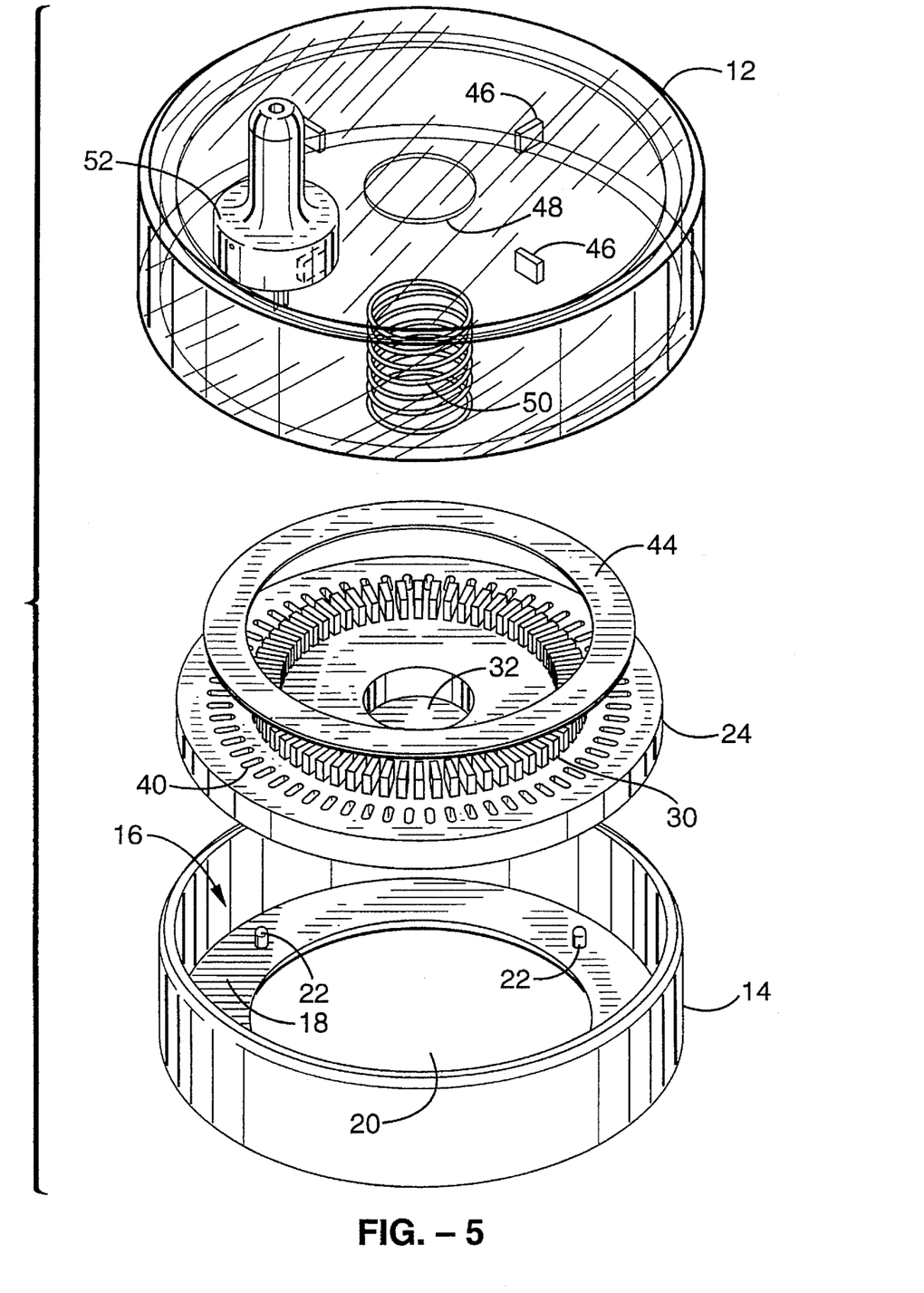
FIG. 5 is an exploded view of an alternative embodiment of the apparatus shown in FIG. 1.

Referring now to FIG. 5, an alternative embodiment of the present invention is shown in which medicament receptacles 40 are integrated into carriage 24. This embodiment of the apparatus operates in the same manner as described above, except that carriage 24 must be replaced when all of the medicament has been administered. Alternatively, the apparatus could be made as a disposable device.

To assist the patient in determining how many doses of medicament have been administered and/or how many doses of medicament remain, cover 12 can be made from a transparent material to permit the patient to directly view the medicament receptacles 40. Alternatively, cover 12 could be made from a non-transparent material with a window being included for viewing of the medicament receptacles. Other indicating methods, such as numbering and color coding the medicament receptacles, could also be employed.

Figure 6:
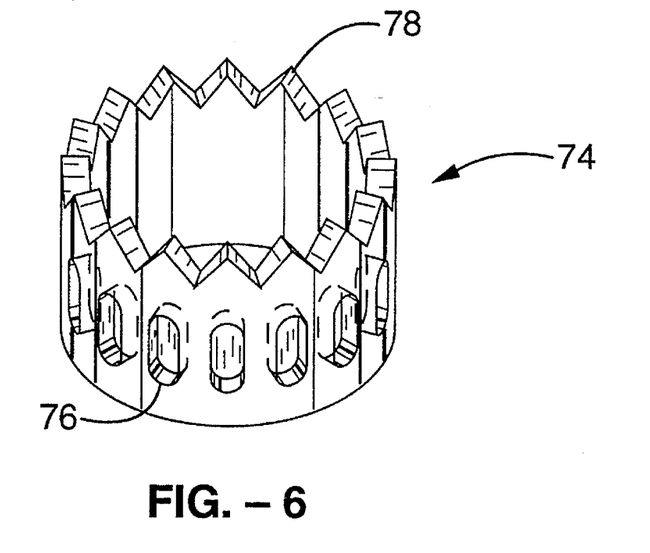
FIG. 6 is an alternative embodiment of the medicament carrier portion of the apparatus shown in FIG. 2.
Figure 7:
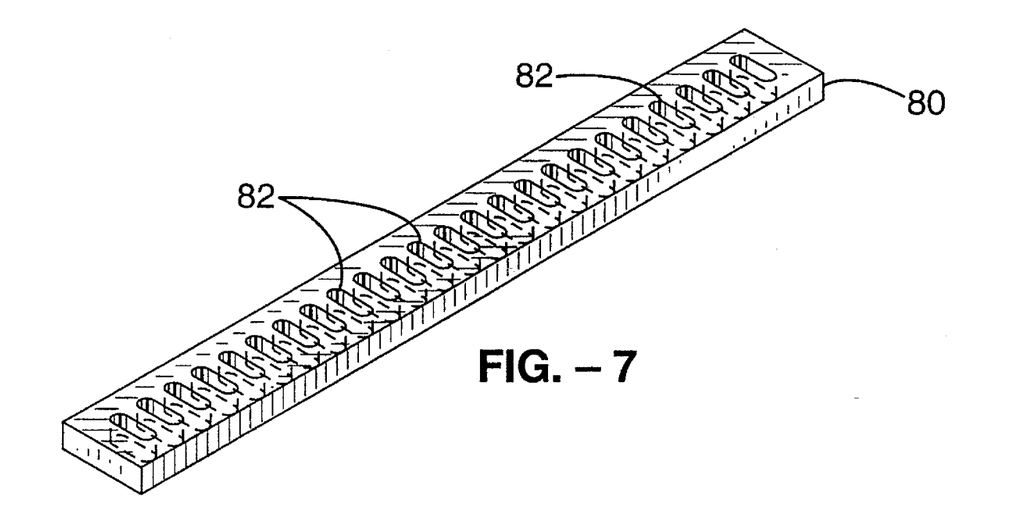
FIG. 7 is a second alternative embodiment of the medicament carrier portion of the apparatus shown in FIG. 2.

Note also that, while the preferred embodiment utilizes a generally circular carriage and ring-shaped medicament carrier, other configurations could be employed without departing from the invention as disclosed herein. For example, referring to FIG. 6, a generally cylindrical crown carrier 74 is shown. In this embodiment medicament receptacles 76 are positioned on the outer surface of crown carrier 74, and there are a plurality of positioning teeth 78 corresponding to medicament receptacles 76 for alignment with the aerosolization conduits which would enter the medicament receptacles from the side. Referring to FIG. 7, a strip carrier 80 is shown with a plurality of medicament receptacles 82. Strip carrier 80 could be threaded through a slot or employed in a "clip" which would be loaded into a housing or other suitable structure.

Accordingly, it will be seen that this invention provides for aerosolization within the medicament receptacle itself, which serves as an aerosolization chamber as well as a receptacle for storage of powdered medicament. Although the description above contains many specificities, these should not be construed as limiting the scope of the invention but as merely providing illustrations of some of the presently preferred embodiments of this invention. Thus the scope of this invention should be determined by the appended claims and their legal equivalents.

I claim:

1. An apparatus for administering medicaments, comprising:
   (a) a housing;
   (b) a medicament carrier, said medicament carrier rotatably coupled to said housing;
   (c) a plurality of medicament receptacles, said medicament receptacles disposed in said medicament carrier, each said medicament receptacle comprising an aerosolization chamber;
   (d) seal means for sealing said each said medicament receptacle; and
   (e) means for aerosolizing medicament internal to a selected one of said medicament receptacles and delivering said aerosolized medicament to a patient, said means including an air inlet conduit and an aerosol outlet conduit, said conduits having a first position wherein said conduits are retracted in relation to said medicament receptacles, said conduits having a second position wherein said conduits extend through said sealing means into said aerosolization chamber in said selected one of said medicament receptacles, wherein medicament contained in said selected one of said medicament receptacles is aerosolized within said aerosolization chamber in said medicament receptacle by inhaled air flowing through said air inlet conduit and delivered to a patient through said aerosol outlet conduit.

2. An apparatus for administering powdered medicaments to a patient, comprising:
   (a) a housing;
   (b) a medicament carrier, said medicament carrier rotatably coupled to said housing;
   (c) a plurality of medicament receptacles, said medicament receptacles disposed in said medicament carrier, each said medicament receptacle comprising an aerosolization chamber;
   (d) seal means for sealing said each said medicament receptacles; and
   (e) means for aerosolizing medicament within a selected one of said medicament receptacles and preventing non-aerosolized medicament from escaping from said medicament receptacle, said means including an air inlet conduit and an aerosol outlet conduit, said conduits having a first position wherein said conduits are retracted in relation to said medicament receptacles, said conduits having a second position wherein said conduits extend through said seal means into said aerosolization chamber in said selected one of said medicament receptacles, wherein medicament contained in said selected one of said medicament receptacles is aerosolized within said aerosolization chamber in said medicament receptacle by inhaled air flowing through said air inlet conduit and delivered to a patient through said aerosol outlet conduit.

3. An apparatus for entraining medicaments in a flow of air, comprising:
   (a) a housing;
   (b) a medicament carrier, said medicament carrier rotatably coupled to said housing;
   (c) a plurality of medicament receptacles, said medicament receptacles disposed in said medicament carrier, each said medicament receptacle comprising an aerosolization chamber;
   (d) seal means for sealing said each said medicament receptacles; and
   (e) means for introducing air flow into a selected one of said medicament receptacles, aerosolizing medicament in said air flow internal to said medicament receptacle, and delivering said aerosolized medicament to a patient, said means including an air inlet conduit and an aerosol outlet conduit, said conduits having a first position wherein said conduits are retracted in relation to said medicament receptacles, said conduits having a second position wherein said conduits extend through said seal means into said aerosolization chamber in said selected one of said medicament receptacles, wherein medicament contained in said selected one of said medicament receptacles is aerosolized within said aerosolization chamber in said medicament receptacle by inhaled air flowing through said air inlet conduit and delivered to a patient through said aerosol outlet conduit.

4. A fixed dose medicament inhalation apparatus, comprising:
   (a) containment means for containing a plurality of predetermined dosages of medicament, said containment means including a plurality of medicament receptacles, each said medicament receptacle comprising an aerosolization chamber;
   (b) seal means for sealing each of said medicament receptacles;
   (c) a housing, said containment means rotatably coupled to said housing about an axis extending coaxially through said containment means;
   (d) air inlet means for puncturing said seal means and introducing air flow into a selected one of said medicament receptacles and aerosolizing medicament internal to said aerosolization chamber of a selected one of said medicament receptacles; and
   (e) aerosol outlet means for puncturing said seal means and delivering aerosolized medicament to a patient from said aerosolization chamber of said selected one of said medicament receptacles;
   (f) said air inlet means and said aerosol outlet means having a first position wherein said air inlet means and said aerosol outlet means are retracted in relation to said medicament receptacles, said air inlet means and said aerosol outlet means having a second position wherein said air inlet means and said aerosol outlet means extend through said seal means into said aerosolization chamber in said selected one of said medicament receptacles, wherein medicament contained in said selected one of said medicament receptacles is aerosolized in said aerosolization chamber in said medicament receptacle by inhaled air flowing through said air inlet means and delivered to a patient through said aerosol outlet means.

5. An apparatus for aerosolizing medicament for delivery to a patient, comprising:

(a) a housing;

(b) a medicament carrier rotatably disposed within said housing, said medicament carrier including a plurality of medicament receptacles, each said medicament receptacle comprising an aerosolization chamber, said each said medicament receptacle covered by a seal;

(c) an air inlet conduit;

(d) an aerosol outlet conduit; and (e) means for penetrating the seal covering a selected one of said medicament receptacles and inserting said air inlet conduit and said aerosol outlet conduit into said aerosolization chamber of said medicament receptacle, said conduits having a first position wherein said conduits are retracted in relation to said medicament receptacles, said conduits having a second position wherein said air inlet conduit and said aerosol outlet conduit extend into said aerosolization chamber in said selected one of said medicament receptacles through its corresponding seal, wherein medicament contained in said medicament receptacle is aerosolized by inhaled air flowing through said air inlet conduit and delivered to a patient through said aerosol outlet conduit, said aerosolization being internal to said medicament receptacle.

6. An apparatus as recited in claim 5, wherein said medicament carrier comprises a carriage and a ring-shaped member, said ring-shaped member detachably coupled to said carriage, said plurality of medicament receptacles disposed in said ring-shaped member.

7. An apparatus as recited in claim 5, further comprising a mouthpiece coupled to said housing, said air inlet conduit and said aerosol outlet conduit extending through said mouthpiece and into said housing.

8. An apparatus as recited in claim 5, further comprising means for aligning said medicament receptacles with said air inlet conduit and said aerosol outlet conduit.

9. An apparatus as recited in claim 5, further comprising means for preventing rotation of said medicament carrier when said air inlet conduit and said aerosol outlet conduit are inserted into said medicament receptacle.

10. An apparatus as recited in claim 5, wherein said housing comprises:

(a) a base, said base including a cavity, said medicament carrier disposed within said cavity and rotatably coupled to said base; and (b) a cover, said cover coupled to said base.

11. An apparatus for aerosolizing medicament for delivery to a patient, comprising:

(a) a base, said base including a cavity;

(b) a cover, said cover detachably coupled to said base;

(c) a medicament carrier, said medicament carrier disposed within said cavity and rotatably coupled to said base;

(d) a plurality of medicament receptacles, said medicament receptacles disposed in said medicament carrier, each said medicament receptacle comprising an aerosolization chamber, said each said medicament receptacle having a seal;

(e) an air inlet conduit, said air inlet conduit coupled to said cover;

(f) an aerosol outlet conduit, said aerosol outlet conduit coupled to said cover; and (g) a spring, said spring disposed between said cover and said medicament carrier, whereby compression of said cover and said medicament carrier compresses said spring and injects said conduits into a selected one of said medicament receptacles;

(h) said conduits having a first position wherein said conduits are retracted in relation to said medicament receptacles, said conduits having a second position wherein said conduits extend into said aerosolization chamber in said selected one of said medicament receptacles through said seal, wherein medicament contained in said selected one of said medicament receptacles is aerosolized in said aerosolization chamber in said medicament receptacle by inhaled air flowing through said air inlet conduit and delivered to a patient through said aerosol outlet conduit.

12. An apparatus as recited in claim 11, wherein said medicament carrier comprises a carriage, said carriage rotatably coupled to said base, and a ring-shaped member, said ring-shaped member coupled to said carriage, said plurality of medicament receptacles disposed in said ring-shaped member.

13. An apparatus as recited in claim 11, further comprising a mouthpiece coupled to said cover, said first and second conduits extending into said mouthpiece.

14. An apparatus as recited in claim 11, further comprising means for aligning said medicament receptacles with said first and second conduits.

15. An apparatus as recited in claim 11, further comprising means for preventing rotation of said medicament carrier when said cover and said medicament carrier are compressed.

* * * * *